United States Patent [19]

Christiansen

[11] 4,157,388

[45] Jun. 5, 1979

[54] HAIR AND FABRIC CONDITIONING COMPOSITIONS CONTAINING POLYMERIC IONENES

[75] Inventor: Arvid Christiansen, Basking Ridge, N.J.

[73] Assignee: The Miranol Chemical Company, Inc., Irvington, N.J.

[21] Appl. No.: 809,484

[22] Filed: Jun. 23, 1977

[51] Int. Cl.² .................. A61K 7/06; A61K 7/08; D06M 15/12
[52] U.S. Cl. .................... 424/70; 8/127.5; 8/127.51; 8/127.6; 8/128 R; 8/128 A; 252/DIG. 2; 252/DIG. 3; 252/8.8; 260/29.2 N; 424/DIG. 2; 424/71; 424/78; 528/367; 528/390; 528/425
[58] Field of Search .................. 424/DIG. 2, 70, 71, 424/78; 252/DIG. 2, DIG. 3, 8.8, R, DIG. 13, DIG. 14; 260/29.2 N, 77.5 C, 552 R, 553 R; 8/127.5, 127.51, 127.6, 128 R, 128 A

[56] References Cited

U.S. PATENT DOCUMENTS

| | | | |
|---|---|---|---|
| 2,761,852 | 9/1956 | Lehmann et al. | 260/77.5 C |
| 2,779,686 | 1/1957 | Kleiner et al. | 260/77.5 C |
| 2,963,465 | 12/1960 | van der Kerk | 260/77.5 C |
| 2,973,342 | 2/1961 | Inaba et al. | 260/77.5 C |
| 3,185,656 | 5/1965 | Gabler et al. | 260/77.5 C |
| 3,390,137 | 6/1968 | Kirshenbaum et al. | 260/77.5 C |
| 3,560,610 | 2/1971 | Korden | 424/72 |
| 3,678,157 | 7/1972 | Kalopissis et al. | 424/71 |
| 3,849,548 | 11/1974 | Grand | 424/70 |
| 3,874,870 | 4/1975 | Green et al. | 424/78 X |
| 3,875,071 | 4/1975 | Grand | 252/106 |
| 3,875,111 | 4/1975 | Tsuda et al. | 260/47 CZ |
| 3,987,162 | 10/1976 | Scheuermann | 424/70 |
| 4,007,005 | 2/1977 | Patel | 8/127.51 |

*Primary Examiner*—James O. Thomas, Jr.
*Assistant Examiner*—Vera C. Clarke
*Attorney, Agent, or Firm*—Ladas, Parry, Von Gehr, Goldsmith & Deschamps

[57] ABSTRACT

Novel polycationic or polyguaternary ammonium ionenes, which generally are hygroscopic, and processes for their preparation, are described. The compounds are useful as conditioning agents for skin, hair, textile products and powders.

4 Claims, No Drawings

HAIR AND FABRIC CONDITIONING COMPOSITIONS CONTAINING POLYMERIC IONENES

BACKGROUND OF THE INVENTION

1. Field of the Invention

This invention relates to conditioning agents for skin, hair, textile products and powders, to processes for their preparation and to their use. The compounds of this invention are polycationic, or polyquaternary ammonium ionenes, which generally are hygroscopic.

2. Description of the Prior Art

Heretofore, polymeric cationic materials, such as those described in U.S. Pat. Nos. 3,875,071 and 3,472,840, have been advocated for use as conditioning agents, for instance, in shampoo formulations. A commercialized product of U.S. Pat. No. 3,472,840, Polymer JR ® (Union Carbide), a quaternary nitrogen-containing cellulose ether, is difficult to use because of its limited compatability with anionic and amphoteric systems. As it is a powdered, cellulosic derivative, special care must be used in dissolving it to produce a uniform, homogeneous solution. Nevertheless, because the demand for conditioning shampoos during the last few years has been considerable, the use of Polymer JR ® in shampoos has increased substantially.

The compounds of the present invention are generally liquids at ordinary temperatures. They mix and dissolve readily with, and are compatible with, most types of shampoo formulations. They seem to act in conjunction with anionic and with some amphoteric surfactants.

SUMMARY OF THE INVENTION AND DESCRIPTION OF THE PREFERRED EMBODIMENTS

The compounds of the present invention are excellent conditioning agents, for instance, in shampoos or cream rinses. They are skin moisturizers, for instance, for use in skin creams. They are also general antistats and humectants for fibrous textile products such as rayon and fiber glass, and are anti-dusting agents for powders and anti-static agents for textile and rug products in general. The compounds of the present invention are also effective as wash cycle conditioners and rewetting agents in some laundry detergent formulations and as agents for binding anionic dyes to fibrous substrates.

In one of its embodiments, the present invention relates to a new and novel way of treating fibrous materials so as to impart better hand, feel, manageability or conditioning properties to them. Said embodiment consists of the use of novel cationic polymers conjunctively acting with fatty anionic materials to achieve these effects.

The compounds of the present invention have molecular weights of at least 350. Although it is preferred that the compounds of the present invention have a large molecular weight, the molecular weight is not critical. The compounds of the present invention are of the formula $$W-(A_1-B_1)_{n1}-Z_1-(B_{11}-A_{11})_{n11}-X_1-(A_2-B_2)_{n2}-Z_2-(B_{22}-A_{22})_{n22}-X_2-(A_3-B_3)_{n3}\cdot\cdot\cdot-X_N-(A_N-B_N)_{nN}-Z_n-(B_{NN}-A_{NN})_{nNN}-Y \quad I$$

wherein W and Y are residues of dihalides, preferably dichlorides, or are the residues of the same or different monohalide chain terminating groups (a chain terminating group is also referred to as a capping group) or may be absent.

Z is an amine residue chain terminating group or quaternium ammonium group, or is a diamine, or diquaternary ammonium group, coupling together two halide residues, or may be the same as any $A_i$ or $A_{ii}$.

X is a halide residue chain terminating group or is the residue of a dihalide coupling together two tertiary amine residues, or may be the same as any $B_i$ or $B_{ii}$.

N may be any number from 4 to ∞;
$A_1$ may equal $A_{11}$ may equal $A_2$ may equal $A_{22}$ etc.;
$B_1$ may equal $B_{11}$ may equal $B_2$ may equal $B_{22}$ etc.;
any one of or all of $n_1 \ldots n_N$ range from 0 to ∞,
and any one or all of $n_{11} \ldots n_{NN}$ range from 0 to ∞;
if $n_i$ is 0, $Z_i$ may or may not be 0;
if $Z_i$ is 0, $n_{ii}$ is 0 and $X_i$ is 0 (note that i ranges from 0 to N),
if $X_i$ is 0, $n_i+1$ is 0 and $Z_i+1$ is 0,
if $n_{NN}$ is 0, Y may or may not be 0.

The compounds of this invention may be prepared by the copolymerization of one or more monomers (A) with one or more monomers (B).

Monomer (A) is a ditertiary amine selected from the group consisting of compounds of the formulae

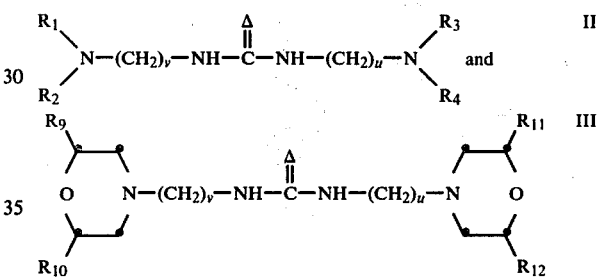

Wherein Δ is selected from the group consisting of S and O,
wherein $R_1$, $R_2$, $R_3$, $R_4$, $R_9$, $R_{10}$, $R_{11}$ and $R_{12}$ may be the same or different and are selected from the group consisting of —H, —CH₃,

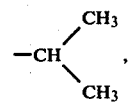

—CH₂CH₃, —CH₂CH₂OH and —CH₂CH₂(OCH₂CH₂)ₓOH wherein x may be 0 to 6 and v and u may be the same or different and each may be 1 to 6, with the proviso that $R_1$, $R_2$, $R_3$ and $R_4$ may not be hydrogen.

These ditertiary amines may be formed by reaction of two moles of a diamine containing one tertiary amine group and either one primary or one secondary amine group (preferably an amine having one tertiary and one primary amine group, especially dimethylaminopropylamine) with one mole of urea or thiourea with the removal of ammonia.

Preferred compounds of monomer A are those of the formula II wherein v is 3 and $R_1$, $R_2$, $R_3$ and $R_4$ are the same and are selected from the group consisting of methyl, ethyl or hydroxyethyl; those of the formula II wherein v is 2 and $R_1$, $R_2$, $R_3$ and $R_4$ are the same and are methyl; and those of the formula III wherein v is 2 or 3 and $R_9$, $R_{10}$, $R_{11}$ and $R_{12}$ are the same and are selected from the group consisting of methyl, ethyl and hydrogen.

(B) is a dihalide selected from the group consisting of compounds of formulae $Cl—CH_2CH_2—O—CH_2CH_2—Cl$, $Cl—CH_2CH_2—O—CH_2—CH_2—O—CH_2CH_2—Cl$, $Cl—CH_2CH_2—Cl$ and $Br—CH_2CH_2—Br$.

$A_i$ and $A_{ii}$ are residues resulting from reacting A with at least one halide group. Thus, although A is a di-tertiary amine, $A_i$ or $A_{ii}$ are either diquaternary ammonium halides or contain one quaternary ammonium halide group and one unreacted tertiary amine group. Depending on the pH of the medium, the tertiary amine group may be present as a salt, for instance, of mineral acids such as phosphoric, sulfuric, hydrochloric or organic acids such as acetic, citric or glycolic acids.

$B_i$ and $B_{ii}$ are residues resulting from reacting B with at least one amine group, by displacing either one or two halide atoms with the equivalent number of amine groups.

The polymer of the present invention may be terminated deliberately with chain terminating agents. These agents are not crucial to the invention. If an excess of monomer (B) is used and a halide is to be capped, monotertiaryamines such as trimethylamine, triethanolamine etc. may be used. If an excess of monomer (A) is used, and a tertiary amine is to be capped or quaternized, monohalides such as 2-chloroethanol, methylchloroacetate, ethylchloroacetate, sodium chloroacetate, alkyl chlorides, methyl β-chloropropionate, epichlorohydrin, ethylenechlorohydrin and sodium β-chloropropionate may be used. Thus, for example, a chain terminating group adjacent to $A_i$ could be the fragment of $R_8$- halogen represented as $R_8$-, and a chain terminating group adjacent to $B_i$ could be represented as

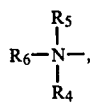

wherein $R_{5-8}$ may be the same as $R_{1-4}$ defined above or just about any alkyl or aryl groups.

Monomers (A) may be prepared by condensing one mole of thiourea or urea with two moles of an appropriate diamine, such as dimethylaminopropylamine, while driving off ammonia gas, as shown below.

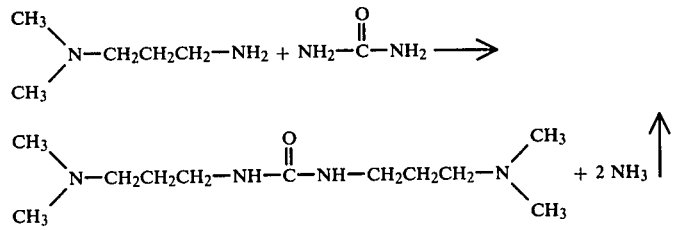

Generally, the monomer (A) is formed by heating together the two components at elevated temperatures, removing ammonia with vacuum or bubbling a gas such as air or nitrogen through the reaction mass. Temperatures as high as 180° C., may be reached. The progress of the reaction may be followed by monitoring the ammonia evolved, or by analyzing the material for primary and tertiary amine. Monomer (A) then may be dissolved in water, in alcohol or in a suitable solvent, and condensed with a monomer (B) to form the polymer. Alternatively, the reaction may be done neat. Toward the end of the reaction period, chain terminating agents may be added if appropriate. This reaction usually is done at an elevated temperature, for example, from 35° to 120° C. Its progress may be followed by analyzing for free halide ion or for tertiary amine. A chain terminating agent may be added to control the molecular weight of the polymer or to alter the characteristics of the polymer. It may be added to completely react pendent B groups, for instance, to ensure that no covalently bound halide, which may be physiologically unsafe, remains. Terminating pendent B groups with tertiary amines increases the quaternary ammonium (cationic) content of the polymers. Terminating pendent A groups with Z groups transforms a tertiary amine group to a quaternary group, which is an advantageous change. If the polymer contains a terminal covalent halogen, it could be capped. If a primary amine is used to cap the polymer, the amine should then be cross-linked.

Molecular weights of about 2,000 to 40,000, appear to have been obtained but they may be perhaps as low as 350 or as high as 100,000.

The monomer "A" is not effective as a conditioning agent nor is the compound B—A—B
where B is $Cl—CH_2CH_2—O—CH_2—CH_2—$
or $Cl—CH_2CH_2—O—CH_2CH_2—O—CH_2CH_2—$
However other compounds B—A—B may be slightly effective. Generally, compounds of the present invention that have at least three cationic groups are effective conditioning agents. Three cationic groups would, for example, be achieved with A—B—Y. Four could be achieved with Z—B—A—B—Z, or A—B—A—B. A—B—A has two quaternary and two tertiary amine groups, and in some cases is effective. There is no upper limit on the molecular weights of the polymer. However, in practice, molecular weights of in excess of $1 \times 10^5$ would be difficult to achieve.

Segments of similar but different polymers may be joined by chain extension agents to form polymers such as described above.

Similarly, block polymers may be used as exemplified by the following:

$$(A_1—B_1)_{n1}—(A_2—B_2)_{n2}$$

where $A_1$ and $A_2$ may be the same or different, and $B_1$ and $B_2$ may be the same or different.

In shampoos, the compounds of the present invention, by themselves have little effect, or a not significant effect. However, the compounds are effective when fatty anionic materials are present. This may be because the polymers act by forming more or less water insoluble complexes with fatty anionic materials, which complexes then plate-out onto the hair (or other substrate). A formula of a typical complex might be the following:

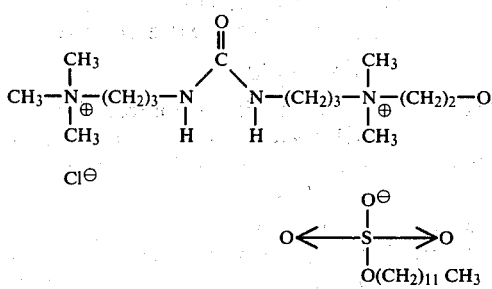
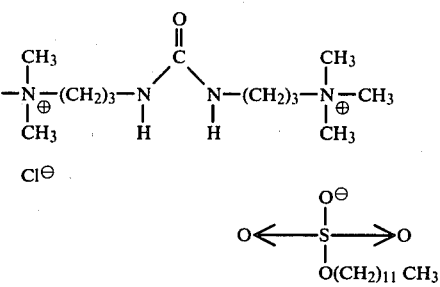

PREPARATIONS AND PROCEDURES

The following preparations and procedures are referred to in the Examples:

Hair Tress Preparation

A bundle of virgin hair of approximately 50 grams is untied and spread out so as to have easy access to small amounts of hair, and is aligned to keep the tops of the hair facing in one direction. A sample of 1.8 to 2.2 g. of hair is removed. A small amount of Duco ® Cement is placed on the center of an oaktag square. The sample of hair is smoothed out and the top of the tress is placed into the Duco ® Cement. The Cement, acrylate material, is spread with a spatula so that the top of the tress is fanned out to give an even distribution of hair on the card. The mounted tress is allowed to dry for 30 minutes. One bundle of hair yields 20 to 25 tresses.

CONDITIONING EFFECTS OF AGENTS ON HAIR

This procedure may be used to test the conditioning or cream rinse effects of treating agents for hair such as shampoos and cream rinses.

Materials

1. Hair Tresses. Either chemically damaged or virgin hair may be used.
2. Hard Rubber Comb. It is desirable to have one comb for each tress used in the study.
3. Tress Anchoring or Clamping Device.

Procedure

Three tresses are used for each product to be tested and three are used as blanks. Dry, untreated tresses are combed to remove knots and loose hair. They are soaked with water, and excess water is removed by blotting with clean toweling. Then 0.5 ml. of treating agent is placed onto one tress and worked well into the hair for about ten seconds, using a circular motion of the hands to moderately tangle the hair. The tress is rinsed in luke warm water and about 0.5 ml of the treating agent is reapplied and worked well into the hair with a circular motion. The hair is rinsed thoroughly in luke warm water, then blotted with clean toweling to remove excess water. The tress is then attached to a clamp, letting it hang free.

While the tresses are still wet, they are gently combed from top to bottom and ease of untangling is noted. This property is evaluated using a scale of 0 (not untagleable) to 5 (extremely easily untangled). The tresses are then combed from top to bottom to evaluate ease of wet-combing, and are similarly rated on a scale of 0 (difficult, much drag) to 5 (slippery).

The tresses are allowed to air-dry and then each tress is combed top to bottom, while the ease with which the comb passes through the hair is evaluated. Dry-combability is rated on a scale of 0 (extreme drag) to 5 (slippery).

During the dry-combing evaluation, the feel of the hair is noted and rated on a scale of 0 (poor), 2.5 (good), 5 (excellent).

Each tress is vigorously combed from top to bottom. Fly-away of hair, the extent to which it spreads out, and the attraction of the hair for the comb is noted. From these observations, static is rated on a scale of 0 (extremely high static) to 5 (no static).

For some purposes the total conditioning effect of an agent may be summarized as the sum of the above five evaluations, the maximum possible rating being 25.

CHEMICALLY DAMAGED HAIR

This procedure may be used to uniformly chemically damage hair.

Materials and Chemicals

1. Polyoxyethylene (3) laurylalcohol, (such as Siponic ® L-3, Alcolac, Inc.)
2. Polyoxyethylene (2) oleylalcohol, (such as Alcolac DV-394).
3. Polyoxyethylene (20) sorbitanmonooleate, (such as Tween ® 80, ICI United States, Inc.).
4. Miranol ® C2M-SF CONC., a product of (Miranol Chemical Company, Inc.), a disodium carboxymethylated coco imidazolinium derivative.
5. Ammonium Hydroxide, 28 to 30% Aqueous Solution.
6. Hair Tresses or Hair Bundle
7. Dye Brush.
8. Hydrogen Peroxide, 6% Aqueous Solution.
9. Ammonium Persulfate.

Procedure

The following mixture is sufficient to treat a 50 g. bundle of hair or 20 to 25 tresses.

| Formula A | |
|---|---|
| Siponic ® L-3 | 30.0g. |
| Alcolac DV-394 | 7.5 |
| Tween ® 80 | 82.5 |
| Miranol ® C2M-SF CONC. | 22.5 |
| Ammonium Hydroxide 28% | 7.5 |
| Formula B | |
| hydrogen Peroxide 6% | 150 g. |
| Ammonium Persulfate | 15 |

Formula (A) is prepared. Formula (B) is prepared immediately before use*. (B) is added to (A) and mixed well until the solution is thick. Dry hair is saturated with the mixture and brushed in well with the dye brush. The saturated hair is heated in an oven at 60° C. for 15 minutes, but no longer, as the hair would burn. The hair is cooled to room temperature and the mixture is brushed well into the hair about every ten minutes for 45 minutes. The hair is rinsed well with warm water and shampooed twice with a non-conditioning shampoo. It is then rinsed well and dried.

*This mixture of strong oxidizing agents should be handled with care. It should not be stored overnight.

The following examples serve to illustrate the invention but they are not intended to limit it thereto.

EXAMPLE 1

Monomer (A) N,N¹-bis(dimethylaminopropyl) urea

A 5 liter 3 neck reaction flask fitted with thermometer, stirrer and reflux condenser was charged with 2450 g (24.02 moles) of dimethylaminopropylamine and 722 g. (12.03 moles) of urea. With stirring and heating, air was bubbled through the reaction mass, carrying $NH_3$ gas out and into a sulfuric acid trap. Reflux began at 114° C. Heating was continued for eight hours as the temperature gradually rose to 165° C. At this time, approximately 22.4 moles of sulfuric acid had been neutralized by the ammonia, and the equivalent weight of the product was found to be 115.8 (theoretical=115). The product was a clear, brown liquid.

EXAMPLE 2

Polymer A-15, neat

An aluminum pan was charged with 23.16 g (0.2 equivalents) of the monomer of Example 1, and 14.29 g. (0.2 equivalents) of bis(2-chloroethyl)ether. The pan was then placed into a 50° C. oven where it was kept for 24 hours. The product was a glassy, brittle, amber colored solid, which rapidly picked up moisture from the air, becoming sticky. On standing, this material dissolved in the moisture it picked up from the air to become a free-flowing pourable liquid thought to be a solution of a polymer of the formula

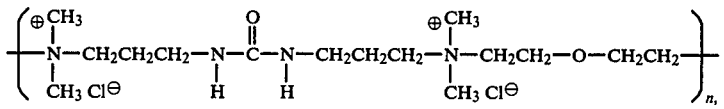

where n is at least one, hereinafter referred to as A-15.

EXAMPLE 3

Polymer A-15, aqueous solution

A 3 neck, 1 liter reaction flask was charged with 115.8 g. (1 equivalent) of the monomer of Example 1 and 187.3 g. of water, and heated to 69° C. At this time, addition of 71.45 grams (1 equivalent) of bis (2-chloroethyl)ether was begun. The temperature was gradually raised to 85° C. over a period of one hour, and the last of the bis(2-chloroethyl) ether was then added. Heating was continued to 99° C., where the reaction mass was held 19 hours and cooled. Reaction was found to be 96.7% complete by chloride ion analysis. The product was an amber colored, clear liquid. 100 grams of water was added to this material, and the mixture was further heated, at a boil, for two hours to distill off 100 ml. of distillate. This "stripping" step removed all traces of unreacted bis(2-chloroethyl)ether. The pH of the clear, amber colored liquid product was 7.75. The solids, by moisture balance determination, was 52%. On standing overnight at room temperature, this material gained 15.4% moisture, a regain of 29.6% based on solids.

EXAMPLE 4

Evaluation of the hair conditioning effect of the polymer of example (3), compared with a commercially available conditioner Polymer JR-400 ® (Union Carbide)

Three shampoo formulations were prepared using Polymer JR-400 ® as the conditioning agent. The formulations were repeated using Polymer A-15 in place of Polymer JR-400 ®. A hair tress study was run in which each formulation (and a water control) was placed on two tresses and then rinsed with water. The effects of applying the formulations to hair were judged for ease of untangling (UNT), wet combability (WC), dry combability (DC) and static (STA). "q.s.", the abbreviation for quantum sufficit, indicates that sufficient water should be added so that the formulation totals 100 parts with water. The three basic formulations were as follow:

| (1) | Miranol ® C2M-SF | 4.0% | active |
|---|---|---|---|
| | Polymer | 2.0 | " |
| | Sodium Polyoxyethylene (3) tridecylsulfate | 9.0 | " |
| | Hamposyl ® L (lauroyl-sarcosine) | 4.0 | " |
| | Water | a.s. | |
| | pH 6.7, adjusted with sodium hydroxide | | |
| (2) | Miranol ® 2MCAS Modified, a dicarboxy methylated coco imidazolinium derivative, lauryl sulfate and polyoxyethylene (3) dodecyl sulfate salts | 17.0% | active |
| | Polymer | 2.0 | |
| | Water | q.s. | |
| | pH 6.7, adjusted with hydrochloric acid | | |
| (3) | Miranol ® C2M-SF | 19.5% | active |
| | Super Amide ® L9C (Lauric diethanolamide (High Active) | 1.9 | " |
| | Foamole ® AR (coconut diethanol-amide (2:1) | 2.0 | " |
| | Polymer | 1.5 | " |
| | Tween 20 (Polyoxyethylene (20) sorbitan Monolaurate) | | |
| | HCl, conc. | 0.8 | " |
| | Water | q.s. | |

The results are summarized in the following table:

TABLE 1

| | Comparison of Shampoo Formulations | | | | | |
|---|---|---|---|---|---|---|
| Formulation | Polymer | Clarity | UNT | WC | DC | STA |
| 1 | A-15 | Clear | 2.25 | 2.40 | 2.50 | 2.90 |
| 1 | JR-400 ® ® | Slightly Hazy | 2.13 | 2.50 | 2.50 | 2.50 |
| 2 | A-15 | Slightly Hazy | 4.50 | 4.50 | 3.38 | 4.00 |
| 2 | JR-400 ® ® | Hazy | 4.00 | 4.13 | 3.50 | 2.75 |
| 3 | A-15 | Clear | 2.75 | 3.50 | 2.75 | 3.50 |
| 3 | JR-400 ® ® | Very Slightly Hazy | 3.25 | 3.75 | 2.88 | 3.00 |

TABLE 1-continued

| | Comparison of Shampoo Formulations | | | | | |
|---|---|---|---|---|---|---|
| Formulation | Polymer | Clarity | UNT | WC | DC | STA |
| $H_2O$ | None | Clear | 1.88 | 2.25 | 2.75 | 3.00 |

The results indicated the following:
1. The polymer of Example 3 (A-15) reduced the static better than Polymer JR-400®.
2. The polymer of Example 3(A-15) showed surprisingly better cream rinse effect than Polymer JR-400®.
3. The wet combability, untangling and dry combability of the polymer of Example 3(A-15) were comparable to that of Polymer JR-400®.

EXAMPLE 5
Co-Reactants

Polymer A-15 was mixed with each of several commercial shampoo ingredients and the mixtures were applied to hair tresses. A material was judged to have interacted with the polymer if desirable properties were conferred on the hair tress that were not conferred on hair tresses by treatment with the polymer itself or with the interacting material itself. The properties considered were wet combability, ease of untangling, dry combability and static. These interactions were considered to be significant if they were measurable by the methods designed to measure the aforementioned properties. The results are summarized in the following table:

Table 2

| Significant Interactions | Slight or no Interactions |
|---|---|
| Hamposyl L® | Ammonyx® LO (lauryl dimethylamine-oxide |
| Miranol® CS Conc. | Lanasan® CL (hydrolized animal protein) |
| Miranol® C2M Conc. | Igepal® CO-630 (polyoxyethylene (g) nonyl phenol) |
| Maprofix® ES (sodium lauryl sulfate) | Deriphat® 151 C |
| Aerosol® OT-75 (dioctyl sodium sulfosuccinate) | Mirataine CB |
| Sandopan® DTC (sodium tridecyl-7 Carboxylated) | |
| Crodafos® SG (polyoxypropylene (5) cetyl ether phosphate) | |
| Maypon® 4C (potassium coco-hydrolized animal protein) | |
| Miranol® C2M-SF Conc. | |

All tests were run at both pH 5 and pH 8 corresponding to the usual limits of the pH range of shampoos. It was observed that every interaction was with an anionic type material, either sulfate, sulfonate, carboxylate or phosphate. No interactions were found with the amine oxide, protein, polyethoxylated material and aminocarboxylic acids. No interaction was found with $Na_2SO_4$.

Thus, the anionic compounds were effective and the non-ionic and some amphoteric compounds were ineffective. Apparently, the Deriphat®, and Mirataine CB, having the formulae

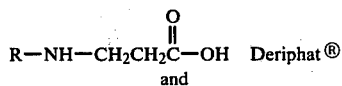 Deriphat® and

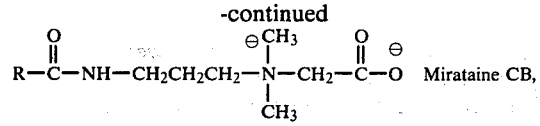 Mirataine CB, present as they were in large excess in the same shampoo formulations with respect to the polymer, detersively lifted the complex from the hair during the shampoo process. In no other case, apparently, was this detersive force stronger than the hair-polymer complex interaction.

EXAMPLE 6

The following procedure was followed in order to determine the degree of irritation the compounds of the present invention would produce when applied to the clipped intact and abraded skin of rabbits. Three healthy, normal, albino rabbits were used for this experiment. On the day prior to the experiment 10% of the total body area of the rabbits was carefully clipped free of all hair. Small animal clippers were used since these left the skin undisturbed. On the posterior of the clipped area several minor abrasions were made so as to penetrate the stratum corneum but not disturb the derma, so that bleeding would be prevented. 0.5 ml. of the test material was patched over the unscarified area. The 2×2 patch area was covered with protective patches and the entire experimental area sealed with surgical tape. The animals were immobilized in racks for a twenty-four hour period. At the end of the twenty-four hour contact period and again forty-eight hours later the treated skin was evaluated according to the method of Draize, as described in "Appraisal of the Safety of Chemicals in Food, Drugs and Cosmetics", published by the Association of Food and Drug Officials of the United States.

The following samples were found to produce no primary irritation:
(1) A 2% solution of the polymer formed by reacting one mole of bis(2-chloroethoxy)ethane with one mole of N,N¹-bis(3-dimethylaminopropyl)urea.
(2) A 2% solution of the polymer formed by reacting two moles of epichlorohydrin and one mole of N,N¹-bis(3-dimethylaminopropyl)urea.
(3) Polymer A-15.

EXAMPLE 7

The following procedure was followed in order to determine if compounds of the present invention produce any irritation when instilled into rabbits' eyes. Three normal, albino rabbits were used in this experiment. The method was that suggested by Draize and described in "Appraisal of the Safety of Chemicals in Foods, Drugs and Cosmetics", published by the Association of Food and Drug Officials of the United States. Each animal had 0.1 ml. of the test sample instilled into the right eye with no further treatment. The untreated left eye of each animal served as its own control. Both the treated and control eyes were examined every twenty-four hours for four days and then again on the seventh day. The scorings recorded were made according to the Draize scale for scoring ocular lesions. Instillation of 0.1 ml. of the four samples referred to above in Example 6 into the right eye of each of the three rabbits, in the manner described did not produce any irritation.

EXAMPLE 8

The following procedure was used in order to determine the toxicity, in mice, of compounds of the present invention. Normal, healthy CFW mice of the Carworth strain, weighing 18 to 21 grams, were used in the study. The test material was administered orally by means of a rigid stomach tube to groups of ten mice at a dosage of 5 ml. of sample per kilo of mouse, each mouse receiving 0.1 cc. of sample. Following the administration of the test sample the mice were observed for seven days. During this time they were maintained in wire cages, 5 to a cage, and had Lab Blox and water ad libitum. The results were as follows:

Table 3

| Sample | Number of Mice Fed | Dead |
|---|---|---|
| 2% solution of Polymer A-15 | 10 | 1 |
| 1% solution of Polymer A-15 | 10 | 0 |
| 1% solution of Polymer JR-400 ® | 10 | 1 |
| It was concluded that Polymer A-15 is no more toxic than Polymer JR-400 ®. | | |

EXAMPLE 9

Polymer A-15 was evaluated as a wash cycle fabric conditioner used together with laundry detergents.

Swatches of untreated wool, nylon taffeta and Dacron-cotton blend fabrics, in a combined weight of 21.5 g, were washed in 500 milliliters of detergent solutions (Tide ® a powdered laundry detergent of Proctor and Gamble containing anionic surfactant sodium carbamate, sodium silicate, sodium sulfate, anti-cakeing and anti-redeposition agents, fabric whiteners and perfume, or Dynamo ®, a liquid heavy duty laundry detergent of Colgate Palmolive at 130° F. for 20 minutes. The swatches then were rinsed for two minutes at 130° F., air dried and evaluated for "hand" and for rewetting. The performance of A-15 in the wash cycle was compared with that of the fabric conditioners Rain Barrel ® (a liquid wash cycle fabric softener of S. C. Johnson & Son) in the wash cycle, Downy ® (a liquid fabric softener of Proctor and Gamble) in the rinse cycle, and with the fatty quaternium ammonium softener Miramine ® TA-30 in the wash cycle.

Table 4

| | Wash Cycle | | Rinse Cycle | | |
|---|---|---|---|---|---|
| Set | Detergent | Conditioner | Conditioner | Rewetting | Conditioning ("hand") |
| 1 | Tide ®, 0.2% | None | None | Fair to Poor | None |
| 2 | " | Rain Barrel ®, 0.15% | " | " | Good |
| 3 | " | None | Downy ®, 0.073% | " | Very Good |
| 4 | " | A-15, 0.15% | None | Good | Good |
| 5 | Dynamo ®, 0.1% | None | " | Fair to Poor | None |
| 6 | " | A-15, 0.5% | " | " | " |
| 7 | " | Miramine ® TA-30, 0.15% | " | " | Good |

This study shows that A-15 is effective as a wash cycle conditioner and rewetting agent in some laundry detergent formulations. It may be noted that Tide ®, with which A-15 is effective, contains an anionic surfactant, whereas Dynamo ®, with which A-15 is inactive, shows slight, if any, reaction with dimethyldihydrogenated tallow quaternary ammonium chloride.

What is claimed is:

1. A hair conditioning composition comprising an effective amount of a compound of the formula

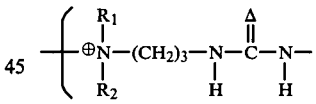

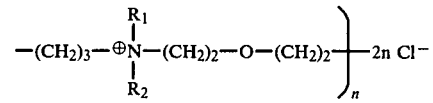

wherein $\Delta$ is selected from the group consisting of S and O, n is at least one and $R_1$ and $R_2$ may be the same or different and are selected from the group consisting of methyl, ethyl, isopropyl, 2-hydroxyethyl and $-CH_2CH_2(OCH_2CH_2)_xOH$ wherein x may be 0 to 6; fatty anionic surfactants, and a conventional carrier agent for hair conditioning compositions.

2. A hair conditioning composition comprising an effective amount of a compound of the formula

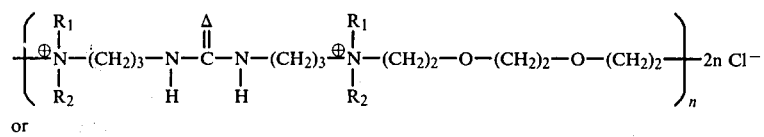

or

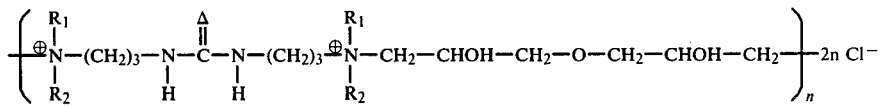

wherein Δ is selected from the group consisting of S and O, n is at least one and $R_1$ and $R_2$ may be the same or different and are selected from the group consisting of methyl, ethyl, isopropyl, 2-hydroxyethyl and —$CH_2CH_2(OCH_2CH_2)_xOH$ wherein x may be 0 to 6; fatty anionic surfactants, and a conventional carrier agent for hair conditioning compositions.

3. A fabric conditioning composition comprising an effective amount of a compound of the formula

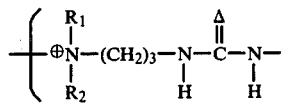

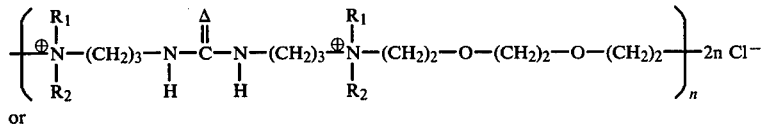

wherein Δ is selected from the group consisting of S and O, n is at least one and $R_1$ and $R_2$ may be the same or different and are selected from the group consisting of methyl, ethyl, isopropyl, 2-hydroxyethyl and —$CH_2CH_2(OCH_2CH)_xOH$ wherein x may be 0 to 6; anionic surfactants, and a conventional carrier agent for fabric conditioning compositions.

4. A fabric conditioning composition comprising an effective amount of a compound of the formula

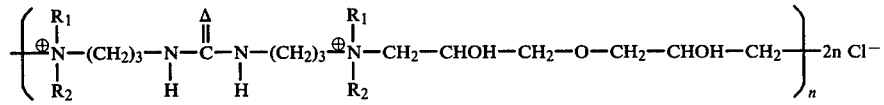

or wherein Δ is selected from the group consisting of S and O, n is at least one and $R_1$ and $R_2$ may be the same or different and are selected from the group consisting of methyl, ethyl, isopropyl, 2-hydroxyethyl and —$CH_2CH_2(OCH_2CH_2)_xOH$ wherein x may be 0 to 6; fatty anionic surfactants, and a conventional carrier agent for fabric conditioning compositions.

* * * * *